United States Patent [19]

Hauck et al.

[11] Patent Number: 4,741,830

[45] Date of Patent: May 3, 1988

[54] SEPARATION MATERIALS FOR THIN LAYER CHROMATOGRAPHY

[75] Inventors: Heinz E. Hauck, Frankfurt am Main; Willi Jost, Langen, both of Fed. Rep. of Germany

[73] Assignee: Merck Patent Gesellschaft mit beschränkter Haftung, Darmstadt, Fed. Rep. of Germany

[21] Appl. No.: 14,162

[22] Filed: Feb. 11, 1987

Related U.S. Application Data

[63] Continuation of Ser. No. 759,551, Jul. 26, 1985, abandoned.

[30] Foreign Application Priority Data

Jul. 28, 1984 [DE] Fed. Rep. of Germany ....... 3427923

[51] Int. Cl.$^4$ .............................................. B01D 15/08
[52] U.S. Cl. .................... 210/635; 210/658; 210/198.3; 210/502.1; 436/162; 502/401; 502/402; 502/439
[58] Field of Search ............ 210/635, 656, 658, 198.3, 210/502.1; 422/70; 436/162; 502/401, 402, 408, 439

[56] References Cited

U.S. PATENT DOCUMENTS

| 4,029,583 | 6/1977 | Chang et al. | 210/502.1 |
| 4,276,061 | 6/1981 | Nestrick | 210/198.3 |
| 4,295,968 | 10/1981 | Halpaap et al. | 210/198.3 |
| 4,324,689 | 4/1982 | Shah | 210/198.2 |
| 4,544,485 | 10/1985 | Pinkerton et al. | 210/656 |

FOREIGN PATENT DOCUMENTS

| 2426306 | 6/1977 | Fed. Rep. of Germany . |
| 2809137 | 1/1983 | Fed. Rep. of Germany . |
| 1580675 | 3/1977 | United Kingdom . |
| 1506226 | 4/1978 | United Kingdom ............. 210/198.2 |

OTHER PUBLICATIONS

Colloid Chemistry of Silica and Silicates by Iler, Cornell University Press, Ithaca, N.Y. 1955, pp. 36–38 relied on.

Patent Office Translation of German Patent No. 2,809,137, PTO-5291 Sep. 1987.

"Recent Developments in the Evaluation of Chemically Bonded Silica Packings for Liquid Chromatography", Journal of Chromatography, 125 pp. 115–127 (1976) by Unger et al.

Primary Examiner—Ernest G. Therkorn
Attorney, Agent, or Firm—Millen & White

[57] ABSTRACT

New separation materials for thin layer chromatography are based on carrier materials coated with an adsorbent silica gel layer which has been surface-modified by a silanizing agent after the coating step. The degree of covering of the modifying reagent can be adjusted in a defined and controllable manner, e.g., from 0.15 to 0.8 $\mu$mol/m$^2$ in the case of reversed phase materials and 1.2 to 2.5 $\mu$mil/m$^2$ in the case of hydrophilic materials. A process for the preparation of these separation materials is also provided.

15 Claims, No Drawings

SEPARATION MATERIALS FOR THIN LAYER CHROMATOGRAPHY

This application is a continuation of application Ser. No. 759,551 filed July 26, 1985, now abandoned.

BACKGROUND OF THE INVENTION

Because of its speed, thin layer chromatography (TLC) is a widely used analytical method. It has been possible to increase its efficiency constantly by continuous further developments and improvement. With the HPTLC technique (high performance thin layer chromatography), it has been possible to achieve results which largely are analogous to those of high pressure liquid chromatography (HPLC). It is thus a rapid and inexpensive alternative to the more time-consuming HPLC analysis, which required more expenditure of equipment. In the end, the advances in the TLC/HPTLC technique are based on improved porous silica gels, which are chiefly used as adsorbents and carrier materials in thin layer chromatography.

In particular, the introduction of silica gel surfaces chemically modified with organic groups (for example, as described in Journal High Resol. Chromatogr. Comm. 3; 215-240, 1980) led to a considerably wider range of applications. It thereby became possible to react the Si—OH groups of the silica gel, which are polar by nature, with suitable Lipophilic or partially Lipophilic organic molecules in a chemical reaction, i.e., to convert them into hydrophobic (reversed phase) or partially hydrophobic groups.

A further enrichment of the TLC technique is in situ modification, that is to say chemical modification on a finished layer of silica gel, for example, as has been described in German Patent Specification No. 2,712,113 or German Patent Specification No. 2,809,137. It is thereby possible to produce, inter alia, homogeneous packing and coating surface structures and purer layers.

In the known preparation processes for chemically modified silica gel, the particular degree of covering of the modified adsorbent with organic groups is predominantly determined by the nature of the groups in the modifying reagent which are capable of undergoing reaction with the Si—OH groups of the silica gel skeleton. To obtain the highest possible degrees of conversion, correspondingly substituted reactive halogenosilanes are usually employed as the modifying reagent. The use of alkoxysilanes which are in themselves slow to react can evidently, according to German Patent Specification No. 2,426,306, lead to quite high degrees of covering of the silica gel surface if catalysts are simultaneously present during the silanization. Although the high degrees of conversion guarantee a good interaction between the hydrophobic carrier matrix and the hydrophobic substance, they mean that the hydrophobically modified layer of silica gel can no longer be wetted by eluting agents and spray reagents containing a large amount of water.

In order to ensure the required wettability with water, the hydrophobic character of the modified layer of silica gel must be reduced. Using less than the stoichiometric amount of halogenosilanes or mixing silica gel with a maximum degree of modification and unmodified silica gel before the coating operation sometimes gives rise to considerable disadvantages, as has been shown in practice. The method usually practiced in which the hydrophobic character of silica gel layers to be modified in situ is reduced by using alkoxy- or aralkoxy-silanes which are slow to react for the chemical modification, frequently has the disadvantage that the degree of covering is greatly reduced. The actual reversed phase effect therefore is frequently only inadequate.

In the case of chemical modification of silica gel layers with organic molecules containing polar-hydrophilic groups, such as, for example, alkyl chains carrying epoxy or amino groups, it is known that, exclusively, the alkoxy- or aralkoxy-silanes which are slow to react can be employed for the modification since the corresponding halogenosilanes do not exist. Silica gel layers modified in this manner accordingly have degrees of covering which are in principle lower, and in some cases too low. A higher surface concentration would be advantageous with this type of modification, however, because, in contrast to the purely hydrophobically modified layers, the layer in any case has the desired wettability with water, even with maximum reaction, because of the groups which have been introduced, some of which are quite polar.

SUMMARY OF THE INVENTION

It is thus an object of this invention to develop a separation material for TLC based on silica gel as the carrier material, which, after modification of the silica gel layer with (hydrophobic) reversed phase materials, has a homogeneous degree of covering which is on the one hand low, and thus enables the layer to be wetted with water, but on the other hand is sufficiently high to enable the reversed phase effect to be effective to the desired degree, so that even quite hydrophobic substances can still be separated by chromatography in an eluting agent system containing water.

It is another object of this invention to satisfy the need to be able suitably to control, by the modification reaction, the degree of covering of the silica get layer which can be wetted with water so that a wide range of applications becomes possible.

It is furthermore an object of this invention to develop hydrophilically modified TLC separation materials, of which the degree of covering, which can likewise be controlled by the modification, is clearly higher than in the case of materials which have been prepared previously e.g., in accordance with German Patent No. 2,712,113 and German Patent No. 2,809,137.

Upon further study of the specification and appended claims, further objects and advantages of this invention will become apparent to those skilled in the art.

It has now been found that pretreatment of the usual HPTLC finished products with solutions of catalysts before the actual in situ modification of the silica gel layer with alkoxy- or aralkoxy-silanes which are slow to react leads to extremely homogeneous degrees of covering of the layer. These are considerably higher than without pretreatment. Moreover, it is possible to carry out the entire process, including the pretreatment, without the exclusion of atmospheric humidity.

It has furthermore been found, surprisingly, that due to the quantitative and, above all, the qualitative compositions of the catalyst solutions, the degree of covering can for the first time be adjusted to the most diverse values in a controllable manner. This effect is not limited only to pure (hydrophobic) reversed phase materials, but can also be utilized for hydrophilic materials, in which higher degrees of surface covering can now be achieved in a controllable manner. The invention thus provides separation materials sized and dimensioned for TLC which can be specifically adapted in an optimum manner to the particular separation problem. By the fine regulation which can be carried out of the proportion of hydrophobic and hydrophilic surface areas on the silica gel layer, together with the possibility of using water-containing eluting agent systems, so that the hydrophobic/hydrophilic interactions can in turn be influenced, outstanding separations by thin layer chromatography can be achieved.

This technical solution, which opens up an abundance of new possibilities for TLC, was not obvious from the state of the art. A process for increasing the surface concentration of the modifying reagent by silanization of pulverulent solids carrying hydroxyl groups in the presence of catalysts, with the exclusion of moisture, is indeed described in German Patent Specification No. 2,426,306; however, the expert can neither see nor conclude from this publication the technical doctrine according to the invention, in particular the controllability of the degree of covering.

This invention accordingly relates to a new separation material for thin layer chromatography which is based on carrier materials coated with adsorbents and comprises a silica gel layer, the surface of which has been modified by silanizing agents after it has been coated onto the carrier, wherein the silica gel surface can be wetted with water and has a uniform degree of covering of 0.15 to 0.8 $\mu mol/m^2$ in the case of reversed phase (RP) materials or 1.2 to 2.5 $\mu mol/m^2$ in the case of hydrophilic materials. Preferred such separation materials have a uniform covering of the water-wettable silica gel layer of 0.3 to 0.5 $\mu mol/m^2$ in the case of reversed phase materials based on C 18-alkyl chains (RP 18) and of 0.35 to 0.7 $\mu mol/m^2$ in the case of reversed phase materials based on C 8-alkyl chains (RP 8), and a separation material which has a uniform covering of 1.5 to 2.3 $\mu mol/m^2$ in the case of hydrophilic materials.

The invention furthermore relates to a process for the preparation of these separation materials, which comprises a procedure in which the silica gel surface which can be wetted with water and is to be modified is homogeneously doped, before treatment with the silanizing agent, by impregnation with a solution of catalysts which are capable of catalyzing silanization reactions of silica gels. A process in which the doping and modification are carried out without the exclusion of moisture is preferred.

A process which comprises a procedure in which a catalyst solution suitable for the desired control of the surface modification has a concentration of preferably 0.01–20% by weight is preferred. Processes which comprise a procedure in which alkoxy- or aralkoxy-silanes are used as the silanizing agents for the preparation of the separation materials according to the invention are furthermore preferred. Moreover, the invention relates to a process for the preparation of separation materials according to the invention in which a mixture of acetyl chloride and glacial acetic acid is preferably used as the catalyst, and a process in which tri-, di- or mono-chloro- or -fluoro-acetic acid is employed as the catalyst.

DETAILED DISCUSSION

Because of their preparation, the separation materials according to the invention have an adjustable defined covering of hydrophobic, hydrophilic and partially hydrophobic/hydrophilic radicals, which is distinguished by high uniformity.

The degree of covering varies from 0.15 to 0.8 $\mu mol/m^2$ in the case of reversed phase materials (RP), preferably 0.3 to 0.5 $\mu mol/m^2$ in the case of reversed phase materials based on C18-alkyl chains and 0.35 to 0.7 $\mu mol/m^2$ in the case of reversed phase materials based on C8-alkyl chains, and 1.2 to 2.5 $\mu mol/m^2$, preferably 1.5 to 2.3 $\mu mol/m^2$, in the case of hydrophilic materials.

The degree of covering of the surface $\tau$ ($\mu mol/m^2$) is defined here in accordance with Kováts (Adv. in Colloid and Interface Science 6, (1976), 95–137). The separation materials according to the invention can also be characterized by their degree of reaction. This is given in % and relates to the maximum degree of covering which can be achieved, which is limited to about 4 $\mu mol/m^2$, above all because of steric influences.

For reversed phase materials, any desired degrees of covering under the maximum degree of covering which can be achieved according to the state of the art can be obtained, the hydrophobic character of the modified silica gel surface being reduced. The separation materials according to the invention thus still have water-wettability in the defined ranges. For hydrophilically modified layers, in which the aliphatic or arylaliphatic chain is thus substituted by polar groups, for example epoxy or amino, separation materials with a degree of covering which can be adjusted to a significantly higher level than was hitherto possible for layers modified in this manner (according to German Patent No. 2,712,113 and German Patent No. 2,809,137) can be obtained.

The range of separation materials for thin layer chromatography is therefore quite considerably increased by the modified silica gel layers according to the invention.

The separation materials according to the invention moreover have the same advantages of the separation materials of German Patent No. 2,712,113 and German Patent No. 2,809,137 which are modified in situ, and are thus distinguished by an outstanding reproducibility, an insensitivity towards the water content of the layer and atmospheric humidity, a high purity of the layer, a homogeneous packing and layer surface structure and fewer problems in preparation, especially on a production scale.

The HPTLC separation materials according to the invention can be prepared in a surprising and extremely simple manner. For this, the finished layers—in contrast to German Patent Specification 2,426,306—are homogeneously doped with catalyst solutions before the actual reaction with silanes.

Suitable catalysts are in principle all those which are known to be capable of catalyzing silanization reactions of silica gels. A wide range is available to the expert from the relevant literature, and suitable examples are inorganic and organic acids, reactive derivatives thereof and inorganic and organic bases. Inorganic and organic acids and reactive derivatives thereof are preferably employed. Substituted organic acids are also most suitable.

Specific examples which may be mentioned of the possible inorganic acids are: HCl, HBr, HI, HF, $H_2SO_4$, $HNO_3$, $H_3PO_4$, $H_3BO_3$, $HClO_4$, $HBrO_4$, $HIO_4$ of mixtures of two or more individual components. All the hydrogen halides are particularly suitable. Examples of possible organic acids are carboxylic acids or substituted carboxylic acids, sulfonic acids or amino acids, but preferably carboxylic acids and their substitution derivatives, mixtures of various individual components also being possible. Preferred examples which may be mentioned of possible carboxylic acids and substituted carboxylic acids are: formic acid, acetic acid, propionic acid, butyric acid, valeric acid, caproic acid, mono-, di- or tri-chloroacetic acid and mono-, di- and tri-fluoroacetic acid. Acetic acid and the fluorinated and chlorinated acetic acids are particularly preferred.

Particularly suitable reactive derivatives of the preferred carboxylic acids are the acid halides, preferably the chlorides and bromides, such as acetyl chloride or acetyl bromide, and furthermore the corresponding anhydrides, azides or esters.

Mixtures of one or more carboxylic acids and/or one or more reactive acid derivatives, in particular acid halides, are furthermore outstandingly suitable. Specific examples which may be mentioned are catalyst systems consisting of acetyl chloride/acetic acid, acetyl chloride/propionic acid, propionyl chloride/acetic acid, propionyl chloride/propionic acid, acetyl chloride/formic acid, acetyl chloride/butyric acid, butyryl chloride/acetic acid, butyryl chloride/propionic acid, butyryl chloride/formic acid, acetyl chloride/valeric acid, valeryl chloride/valeric acid, propionyl chloride/butyric acid, propionyl chloride/valeric acid, formyl chloride formic acid, formyl chloride/acetic acid, acetyl chloride/acetic acid/propionic acid, acetyl chloride/acetic acid/formic acid, acetyl chloride/propionyl chloride/acetic acid, acetyl chloride/propionyl chloride/propionic acid and acetyl chloride/propionyl chloride/formic acid.

In the mixtures mentioned, instead of the acids, it is also possible to use correspondingly substituted acids, preferably the mono-, di- or tri-fluoro- or -chloro-substituted acids. Catalyst mixtures comprising acetyl chloride and acetic acid are particularly preferred.

The preferred suitable inorganic base is ammonia. Examples which may be mentioned of possible organic bases are pyridine, di- and tri-ethylamine, butylamine and ethylenediamine.

The catalysts can be present in concentrated form, if appropriate in the gaseous or vaporous state, or in solutions, preferably in dilute solutions. Preferred suitable solvents are organic, optionally water-miscible solvents, in particular polar organic solvents, that is to say alcohols, such as, for example, methanol, ethanol, n-propanol, isopropanol, n-butanol and methyl-propyl alcohol, and also acetone, methyl ethyl ketone or less polar solvents, such as dioxane, methylene chloride and di- and tri-chloroethane, or, finally, non-polar solvents, such as benzene, nitrobenzene, toluene, xylene, n-hexane or n-heptane, provided that the catalysts or catalyst components have an adequate solubility in the corresponding solvents or can be adequately mixed with them. The solvents can be employed in the dried state or with certain water contents.

The concentration of the catalyst or of the catalysts in the solvent can be varied between 0.01% to 20% by weight, based on the impregnating solution. The concentration is preferably 0.05 to 10%. In the case of strong acids or bases, a lower concentration is preferably chosen, while a higher concentration is preferably chosen in the case of weak acids or bases. In the case of catalyst mixtures, the ratio of the individual components in relation to one another can be varied within wide limits. Ratios of between 1:9 and 9:1, in particular 1:9, 2:8, 3:7, 4:6, 5:5, 6:4, 7:3, 8:2, and 9:1, are preferably established in two-component systems.

The time of doping with the catalyst solution is between 1 minute and 20 minutes, preferably between 8 and 12 minutes. A silica gel plate is preferably doped in 0.8–1.0 liter of catalyst solution. The water contents established on the surface-active silica gel plates which have not yet been modified do not have an influence on the particular resulting degree of reaction during the modification. Predrying or activation of the plates is not necessary. Atmospheric humidity does not have to be excluded, in contrast to the process of German Patent Specification No. 2,426,306. After predoping of the plates with catalyst solution, either modification is carried out directly, or, preferably, one or more washing operations are carried out, to remove excess catalyst. This is not possible in the process described in German Patent Specification No. 2,426,306. The solvents mentioned are usually employed for the washing processes. The volume of solvent per washing and plate is preferably 0.7–1.0 liter. The plates are preferably exposed to the washing solution for 8–12 minutes per washing. Typically, the plate specific surface area is 500–600 $m^2/g$.

The chemical modification of the silica gel layer which follows the doping with catalyst is carried out in a manner which is known per se (for example German Offenlegungsschrift No. 1,712,113). The modification here proceeds by a process in which the silica gel layer is impregnated or soaked with the silanizing agent. This can be effected, for example, by immersing the starting material in the solution of the silanizing agent or by spraying it with such a solution. A customary solvent which is inert toward the silanizing agent used is employed as the solvent. Solvents which are preferably used are organic solvents with boiling points between 30° and 180° C., for example chlorinated hydrocarbons, such as methylene chloride, chloroform and/or di- and tri-chloroethane, or aromatic or aliphatic hydrocarbons.

The silanizing agents used are alkoxy- or aralkoxysilanes of the $R—SiX_3$ type which are slow to react, wherein R is an unsubstituted alkyl or aralkyl group in the case of (hydrophobic) reversed phase modification or an alkyl or aralkyl group substituted with polar groups in the case of hydrophilic modification. X can be alkoxy, aralkoxy or alkyl, but at least one X per silane molecule must be alkoxy or aralkoxy.

R can contain 1–20 C atoms in the optionally branched alkyl chain, and alkyl chains of 8 or 18 C atoms are preferred. Typically, the aryl portions of R and X contain 6–10 C-atoms. The X alkyl portions contain 1–20 C-atoms also.

If R in the case of hydrophilic modification is substituted by polar groups, examples of possible substituents are hydroxyl, amino, epoxy, cyano, halogen, ammonium, sulfonium and carboxyl. Epoxy or amino groups are preferably employed as substituents. A large number of silanizing agents are known from the literature or can be prepared by methods analogous to known methods. They are suitable for the process according to the invention in the same way as they are suitable for the known modifications of surfaces of adsorbents. The amount of silanizing agent used for the surface modification depends, above all, on the thickness of the layer of silica gel and the specific surface area of the silica gel used for coating. In order to obtain complete covering of the silanol groups accessible on the untreated silica gel, the silanizing agent should be employed in an amount of at least 10 $\mu mol/m^2$ of silica gel surface.

However, an excess of the silanizing agent is preferably used, for example 0.1 to 1 mmol/m². A larger excess can also be advantageous in certain cases. After the impregnation with the silanizing agent, the separation materials are allowed to drip and are then passed through several cleaning baths in order to remove excess silanizing agent and to purify the modified layer. The required washing processes are essentially analogous to the process already described in Patent Specifications Nos. 2,712,113 and 2,809,137.

Starting materials which can be used are all the usual separation materials with a TLC silica gel layer on carriers, that is to say also the high performance separation material such as is described, for example, in German Offenlegungsschrift No. 2,524,065. Carriers which can be used are all the customary materials, glass plates being preferred. However, foils, for example aluminium foil, or plastic films can also be used. The silica gel layer is applied to these carrier materials in the form of a usually aqueous suspension which can be brushed on, using customary brushing apparatuses or coating units. Binders, which increase the adhesion and the abrasion-resistance, and, if appropriate, indicators are also added to this suspension. Preferred binders are the organic binders mentioned in German Patent Specification No. 1,442,446 or in German Auslegeschrift No. 1,517,929. The indicator most frequently used is a fluorescence indicator, preferably magnesium tungstate, which absorbs in the UV at 254 nm (German Patent No. 2,816,574). The binders are as a rule added in amounts of 0.1 to about 10%, and the indicators in amounts of about 0.5 to 5% by weight. The layer thickness of the silica gel layer on the separation materials according to the invention is usually of the order of 100 to 300 μm, as in the TLC separation materials hitherto customary. In exceptional cases or for particular applications, however, separation materials with thinner or thicker layers can also be prepared. The specific surface area of the silica gels is between about 1 and 1,000 m²/g, and is in most cases between 200 and 800 m²/g.

The water-wettability of the modified silica gel layers according to the invention depends, inter alia, on the particular phase with which the layer has been modified. RP-18 materials (unsubstituted straight-chain alkyl with 18 C atoms) can as a rule still be wetted with water at a degree of covering of about 0.55 μmol/m², and RP-8 materials (unsubstituted straight-chain alkyl with 8 C atoms) can still be wetted with water at a degree of covering of about 0.7 μmol/m².

The parameters for controlling the separation materials according to the invention which can be correspondingly adjusted are essentially the nature and composition of the catalyst solutions or catalyst mixtures. Depending on the desired end product, the expert can select the doping conditions or compose the most suitable solutions in each case by routine testing. Table 1 shows the degrees of covering of the separation materials modified according to the invention as a function of the catalysts/solvents, used by way of example in their preparation, in silica gel layers modified in different ways. For comparison, the corresponding values are given for HPTLC separation materials which have been prepared according to German Patent Nos. 2,712,113 and 2,809,137. The conditions given are to be understood purely as examples, and are thus not intended as any limitations. The comparison examples are given as reference.

From Table 1, it can be seen that separation materials with both lower (RP-18, RP-8) and higher degrees of covering (DIOL), in comparison with the state of the art, can be obtained. The very high degree of covering for the DIOL-modified separation material is particularly remarkable.

Table 2 shows that the solvents required for the catalysts can also influence the degree of covering, under otherwise identical conditions. The solvents mentioned are to be taken purely as examples.

Table 3 shows the degrees of covering or reaction of separation materials, during the preparation of which various catalysts, under otherwise identical conditions (Example 2), have been used for the modification. The choice of the catalysts and their concentration is also to be understood purely by way of example here. As can be seen from Table 3, the influence of the nature of the catalyst on the degree of covering of the separation materials according to the invention is of major importance. The degree of covering can thus be accordingly controlled, as is expressed particularly well in the example with chlorinated and fluorinated acetic acid.

Surprisingly, catalyst systems consisting of two or more catalyst components result in a surprisingly wide variance in the controllability of the degree of covering, depending on the ratio with respect to one another in which the individual components are employed. As an example, Table 4 shows the correlation between the ratio of acetyl chloride to acetic acid, both of which can be used individually as catalysts, and the carbon content of an RP-18 HPTLC separation material, which is directly related to the degree of covering. Such catalyst systems frequently show synergistic effects in respect of the degree of covering when their action is compared with that of the individual components.

Since the degree of covering and hence the hydrophobic character of the active silica gel surface can be varied, it is possible to separate a considerably larger number of hydrophobic/hydrophilic substances and substance mixtures by thin layer chromatography. Problem-specific separation materials are thus available. The range of applications can moreover be increased by the possibility of using water-containing eluting agent systems. This also results in an additional fine regulation of the separation properties. The range of applications of thin layer chromatography is thus decidedly increased by the separation materials according to the invention.

Water wettability means under all indicated conditions that, using pure water or high water containing solvents, the hydrophobic repulsion forces of the surface area modified with partially hydrophilic groups are smaller than the capillary forces causing the solvent transport.

The necessary control of the extent of surface coverage, i.e., silanization extent, can also be controlled by varying the time of impregnation for a given catalyst solution within the aforementioned range. The greater the degree of impregnation (the longer the time), of course, the greater the extent of surface coverage, all other conditions being equal. However, in general, it will be preferred to vary the extent of surface coverage by varying the nature of the catalyst solution as described above and than carrying out the impregnation step such that the silica gel becomes substantially saturated with the catalyst to the extent possible for a given solution. Furthermore the extent of silanization can be controlled by conventional modification of the silanization reaction conditions, e.g., the temperature and duration of the silanization reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

The examples given below differ only in the nature and composition of the catalyst used and the nature of the silanes employed.

HPTLC silica get 60 F 254s pre-coated plates, 10×20 cm from E. Merck, Darmstadt, were used in all cases. Glass separation chambers from Desaga were used as immersion containers for all the preparation steps carried out.

The generally applicable preparation plan is as follows:

(a) Doping of the plates with the catalyst or catalyst mixture by immersion in a corresponding solution (b) Immersion of the plates in a corresponding organic solvent to remove excess amounts of catalyst (c) Modification of the plates by immersion in the corresponding silane solution (d) Several successive washing processes by immersion of the plates in corresponding solvents and/or solvent mixtures of different polarity.

EXAMPLE 1

Preparation of an HPTLC RP-18 pre-coated layer which can easily be wetted with water re (a) Doping of an HPTLC silica gel 60 F 254s pre-coated plate with a solution of 0.9 ml of concentrated HCL in 900 ml of methanol (=0.04% HCL) in the course of 10 minutes.

re (b) Intermediate washing operations, each of 10 minutes duration, in 900 ml of methanol and then in 900 ml of toluene.

re (c) Silanisation in 900 ml of a 10% toluene solution of methyloctadecyldimethoxysilane in the course of 20 minutes.

re (d) Washing operations on the plates, each of 10 minutes duration, with 2 900 ml portions of toluene, 900 ml of methylene chloride/methanol (1/1), 2 900 ml portions of acetone/water (1/1) and 900 ml of methanol.

EXAMPLE 2

Preparation of an HPTLC RP-18 pre-coated plate which can still just be wetted with water re (a) Doping of an HPTLC silica gel 60 plate with a solution consisting of 63 ml of acetyl chloride and 27 ml of glacial acetic acid in 900 ml of toluene (ratio of 7:3, total concentration of 10%) in the course of 10 minutes.

re (b) Intermediate washing operations, of 10 minutes duration, with 900 ml of toluene.

re (c) Analogously to Example 1.

re (d) Analogously to Example 1.

EXAMPLE 3

Preparation of an HPTLC RP-18 pre-coated plate which can easily be wetted with water re (a) Doping of an HPTLC silica gel 60 plate with a solution consisting of 81 ml of acetyl chloride and 9 ml of glacial acetic acid in 900 ml of toluene (ratio of 9:1, total concentration of 10%) in the course of 10 minutes.

re (b, c and d) Analogously to Example 2.

EXAMPLE 4

Preparation of an HPTLC RP-8 pre-coated plate which can still just be wetted with water re (a and b) Analogously to Example 2.

re (c) Use of methyloctyldimethoxysilane, otherwise analogously to Example 2.

re (d) Analogously to Example 2.

EXAMPLE 5

Preparation of an HPTLC diol pre-coated plate re (a) Doping of an HPTLC silica gel 60 plate with a solution consisting of 4.5 ml of trichloroacetic acid in 900 ml of toluene (total concentration of 0.5%) in the course of 10 minutes.

re (b) No intermediate washing.

re (c) Silanization with 900 ml of a 10% toluene solution of γ-glycidyloxypropyltrimethoxysilane in the course of 20 minutes.

re (d) Analogously to Example 2.

TABLE 1

| Separation material HPTLC | Catalyst/Solvent | Degree of covering τ (μmol/m$^2$) | Degree of conversion (%) | Reference |
| --- | --- | --- | --- | --- |
| RP-18 | — | 2.05 | 51.0 | German Patent 2,712,113 |
| RP-18 | 0.04% HCl in CH$_3$OH | 0.36 | 9.0 | German Patent 2,809,137 Example 1 |
| | 10% acetyl chloride/ glacial acetic acid (7:3) in toluene | 0.61 | 15.0 | Example 2 |
| RP-8 | — | 2.94 | 77.0 | German Patent 2,712,113 |
| RP-8 | 10% acetyl chloride/ glacial acetic acid (7:3) in toluene | 0.74 | 19.0 | German Patent 2,809,137 Example 4 |
| DIOL | — | 0.64 | 16.3 | German Patent 2,712,113 |
| DIOL | 0.5% trichloroacetic acid in toluene | 1.81 | 46.5 | German Patent 2,809,137 Example 5 |

TABLE 2

| Solvent | Degree of covering τ (μmol/m$^2$) | Degree of conversion (%) |
| --- | --- | --- |
| n-Heptane | 0.31 | 7.8 |
| Toluene | 0.6 | 15.0 |
| Methylene chloride | 0.57 | 14.8 |

TABLE 3

| Catalyst | Degree of covering $\tau$ ($\mu$mol/m$^2$) | Degree of conversion (%) |
| --- | --- | --- |
| 0.04% HCl in methanol | 0.36 | 9.0 |
| 10% acetyl chloride in toluene | 0.18 | 4.5 |
| 10% glacial acetic acid in toluene | 0.25 | 6.2 |
| 10% propionic acid in toluene | 0.18 | 4.5 |
| 10% trifluoroacetic acid in toluene | 1.05 | 26.2 |
| 10% trichloroacetic acid in toluene | 1.01 | 25.2 |
| 10% dichloroacetic acid in toluene | 0.76 | 19.0 |
| 100 g monochloroacetic acid in 1 l of toluene | 0.52 | 13.0 |

TABLE 4

| Acetyl chloride/glacial acetic acid 10% in toluene | 1:9 | 3:7 | 5:5 | 6:4 | 8:2 | 9:1 |
| --- | --- | --- | --- | --- | --- | --- |
| % C | 14.5 | 10.2 | 6.9 | 6.5 | 6.2 | 6.1 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for controlling water wettability from easily wettable to just wettable of a separation material sized and dimensioned for thin layer chromatography and comprising a carrier material coated with an absorbent silica gel layer whose surface has been modified by reaction with a silanizing agent, comprising, prior to the silanization step, homogeneously doping the silica gel surface by completely impregnating it with a solvent solution of a catalyst effective for catalyzing the silanization reaction of the silica gel surface with the silianization agent, said silica gel surface being doped to a preselected extent, solvent washing the resultant doped silica gel layer of excess catalyst prior to the silanization reaction, and adjusting the water wettability of the separation material by adjusting said impregnation step to achieve a degree of covering of the silica gel surface with an amount of catalyst effective to produce a degree of silanization of 0.15–0.8 $\mu$mol/m$^2$ for reversed phase materials or 1.2–2.5 $\mu$mol/m$_2$ for hydrophilic materials, the less the extent of covering the higher the degree of water wettability.

2. A process according to claim 1, wherein the doping and silanization steps are carried out without the exclusion of moisture.

3. A process of claim 2, wherein the doping and silanization steps are carried out in the presence of moisture.

4. A process of claim 1, wherein the extent of the silanization of the silica gel surface is controlled by preselection of at least one of: (a) the composition of the catalyst, (b) the concentration of said solution, (c) the composition of the solvent, or (d) the time of impregnation.

5. A process of claim 4, wherein the catalyst concentration in the impregnating solution is 0.01 to 20% by weight.

6. A process of claim 4, wherein at least one intermediate washing is included between the doping and silanization steps to eliminate excess amounts of catalyst.

7. A process of claim 1, wherein the silanization step renders the silica gel surface hydrophobic but water-wettable.

8. A process according to claim 7, wherein the resultant modifying separation material has a degree of covering of 0.15 to 0.80 $\mu$mol/m$^2$, and the silanization agent is a silane of the R—SiX$_3$ type, wherein R is unsubstituted alkyl, aryl, or aralkyl of 1 to 20 C atoms in the alkyl chain and X is alkoxy or alkyl with 1 to 20 C atoms in the alkyl chain, with the proviso that at least one X is alkoxy or aralkoxy.

9. A process according to claim 8, wherein a mixture of acetyl chloride and glacial acetic acid is used as the catalyst.

10. A process according to claim 8, wherein tri, di- or mono-chloro- or -fluoro-acetic acid is used as the catalyst.

11. A process of claim 1, wherein the silanization renders the silica gel surface hydrophililc, the degree of covering thereof is 1.2 to 2.5 $\mu$mol/m$^2$, and the silanization agent is a silane of the R—Six$_3$ type, wherein R is alkyl, aryl or aralkyl, in each case containing at least one epoxy or amino group, and X is alkoxy or alkyl of 1–20 C atoms in the alkyl chain, with the proviso that at least one X is alkoxy or aralkoxy.

12. A process according to claim 9, wherein the epoxy groups are additionally converted into diol groups by treatment with dilute acid after the modification of the surface.

13. A process according to claim 1, wherein the solvent washing step is performed directly before the silanizing reaction.

14. A process according to claim 1, wherein the amount of said catalyst is effective to produce a degree of silanization of 0.15–0.8 $\mu$mol/m$^2$.

15. A process according to claim 1, wherein the amount of said catalyst is effective to produce a degree of silanization of 1.2–2.5 $\mu$mol/m$^2$.

* * * * *